United States Patent [19]

Miyamoto et al.

[11] 4,015,937

[45] Apr. 5, 1977

[54] PROCESS FOR DETECTING THE COMPLETION OF THE STERILIZING TREATMENT USING A COLOR CHANGING INDICATOR COMPOSITION

[75] Inventors: Kozo Miyamoto; Kunitaka Fujiwara, both of Toyonaka, Japan

[73] Assignee: Sakata Shokai Ltd., Osaka, Japan

[22] Filed: Nov. 14, 1975

[21] Appl. No.: 631,904

[52] U.S. Cl. .................. 23/230 R; 21/DIG. 4; 23/253 TP; 116/114 AM; 252/408; 260/157; 260/158; 260/165

[51] Int. Cl.² .................. G01N 21/06; C09B 29/00

[58] Field of Search ....... 23/230 R, 232 R, 253 TP; 252/408; 21/DIG. 4; 116/114 AM

[56] References Cited

UNITED STATES PATENTS

| | | | |
|---|---|---|---|
| 2,606,654 | 8/1952 | Davis | 116/114 AM |
| 2,798,855 | 7/1957 | Hainsworth | 23/230 R X |
| 2,998,306 | 8/1961 | Huyck et al. | 23/232 R X |
| 3,093,242 | 6/1963 | Huyck | 116/114 AM |
| 3,627,469 | 12/1971 | Cheng | 23/253 TP X |
| 3,684,737 | 8/1972 | Emigh | 23/253 TP X |
| 3,852,034 | 12/1974 | Gunther | 23/232 R |

*Primary Examiner*—Sidney Marantz
*Attorney, Agent, or Firm*—Flynn & Frishauf

[57] ABSTRACT

Process for detecting the completion of a gaseous alkylene oxide sterilization treatment of medical or surgical equipment by the color change of particular azo dye indicators.

20 Claims, No Drawings

PROCESS FOR DETECTING THE COMPLETION OF THE STERILIZING TREATMENT USING A COLOR CHANGING INDICATOR COMPOSITION

BACKGROUND OF THE INVENTION

This invention relates to a process for detecting the completion of a sterilizing treatment using a color changing indicator composition, in case medical and surgical instruments are sterilized with an alkylene oxide, particularly with gaseous ethylene oxide.

Medical materials such as gauzes, bandages, or absorbent cotton, or surgical instruments such as injectors, scalpels, or scissors have hitherto been used after they have been sterilized with dry heat, pressure steam, or by boiling, using a sterilizer in the hospital. However, they have recently been supplied to users (such as hospitals and medical practioners) in a hermetically sealed sterilized style after they have been completely sterilized in the factory of the manufacturer for medical and surgical materials, instead of sterilizing them immediately prior to their use in hospitals or the like. Gaseous sterilization is most suitable for carrying out such sterilizing treatment, and gaseous ethylene oxide is used for this purpose.

This process depends on an improvement of a hermetically sealing material which permits a germ-free state of the hermetical sealing to be maintained after it has been sterilized. Hermetically sealed materials are completely sterilized in the manufacturer's factory on a large scale and supplied to users thereafer, so they may serve for use immediately after they are taken out of the package as they are required. For such hermetically sealed condition, a detection of the completion of the sterilization should, needless to say, be necessary.

As conventional indicator compounds which change in color by the action of gaseous ethylene oxide, such reagents that contain a hydrochloric acid salt of a basic substance together with a pH indicator have generally been used hitherto. The hydrochoric acid salt of the basic substance is reacted with ethylene oxide, to remove the hydrochloric acid. The thus remaining basic substance acts with pH indicator to cause the color change. However, the constancy of such color change is not satisfactory to detect the completion of the sterilizing treatment with accuracy, because the color change may also be caused by contact with a slightly acidic or basic substance in the atmosphere.

Further, indicator compounds having particular characteristics are also known, e.g. compounds having a pyridine ring as represented by 4-(4-nitrobenzyl)pyridine, etc. Such compounds change in color from white to pale blue by a reaction with gaseous ethylene oxide in the presence of an alkaline catalyst. But the extent of the color change, namely, the hue and the strength before and after the gaseous sterilization, are both unsatisfactory and are not suitable for detecting the completion of the sterilization with naked eyes.

The primary object of this invention is to provide a process for detecting the sterilized effect with the naked eye using an indicator composition therefore which changes color distinctly when said sterilization is performed with gaseous ethylene oxide and is stable for atmospheric changes.

Another object of this invention is to provide a process for detecting the sterilized effect of a color changing indicator composition coated or printed on a sealing material used for hermetically sealed medical or surgical materials or instruments with the naked eye by a distinct color change of said composition when said indicator composition is subjected to sterilization together with the instrument with gaseous ethylene oxide.

Other objects and advantages of this invention will clearly be understood from the following description.

SUMMARY OF THE INVENTION

In order to attain the purposes as described hereinbefore, a color changing indicator composition comprising from 1 to 5% by weight of an azo dye, from 10 to 50% by weight of a hydrophobic polymer and from 30 to 85% by weight of a solvent or a mixed solvent, further having from 1 to 5% weight of a catalyst and from 1 to 10% by weight of a filler admixed thereto as an optional ingredient, are used in this invention, and the effect of the sterilization is thus completely assured. All percents by weight are based on the total weight of a color changing indicator composition.

DETAILED DESCRIPTION OF THE INVENTION

The azo dye in said indicator compounds is represented by the following general formula (1)

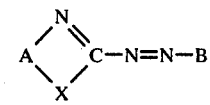

wherein A represents an ethylene residual group, an o-phenylene residual group, or

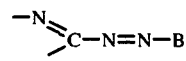

with proviso that —N is linked with X, while —C with N in the formula (1), respectively, which is further enabled to have an undissociative group as a substituent; X represents —S— or

B represents an aniline-derivative residual group which can be coupled to the para-position or an enamine residual group having the formula,

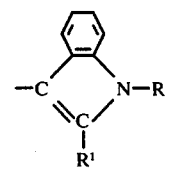

and the both groups are further enabled to have an undissociative group as a substituent, said R represents a hydrogen atom or a lower alkyl group having from 1 to 3 carbon atoms, said $R^1$ represents a hydrogen atom, a lower alkyl group having from 1 to 3 carbon atoms or a phenyl group, said undissociative group represents a lower alkyl group having from 1 to 3 carbon atoms, an alkoxyl group having from 1 to 3 carbon atoms, —$R^2$—OH, chlorine, a phenyl group or a nitro group, wherein $R^2$ represents an alkylene group having from 1 to 3 carbon atoms. Said azo dyes include, for example, the following compounds:
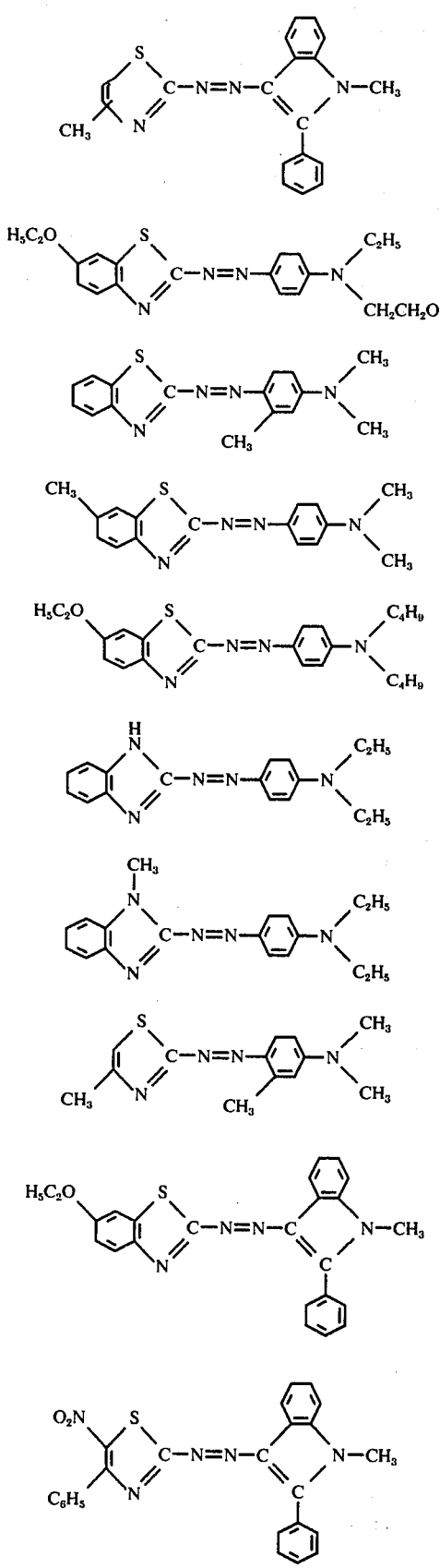
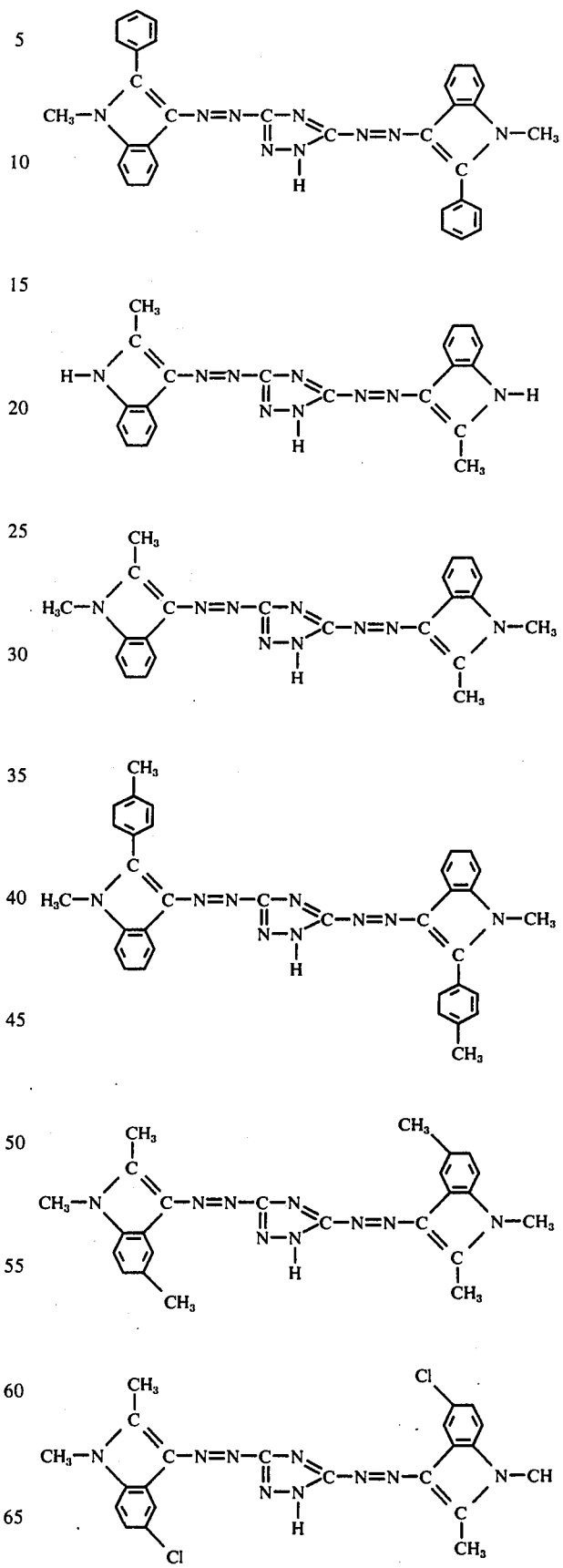

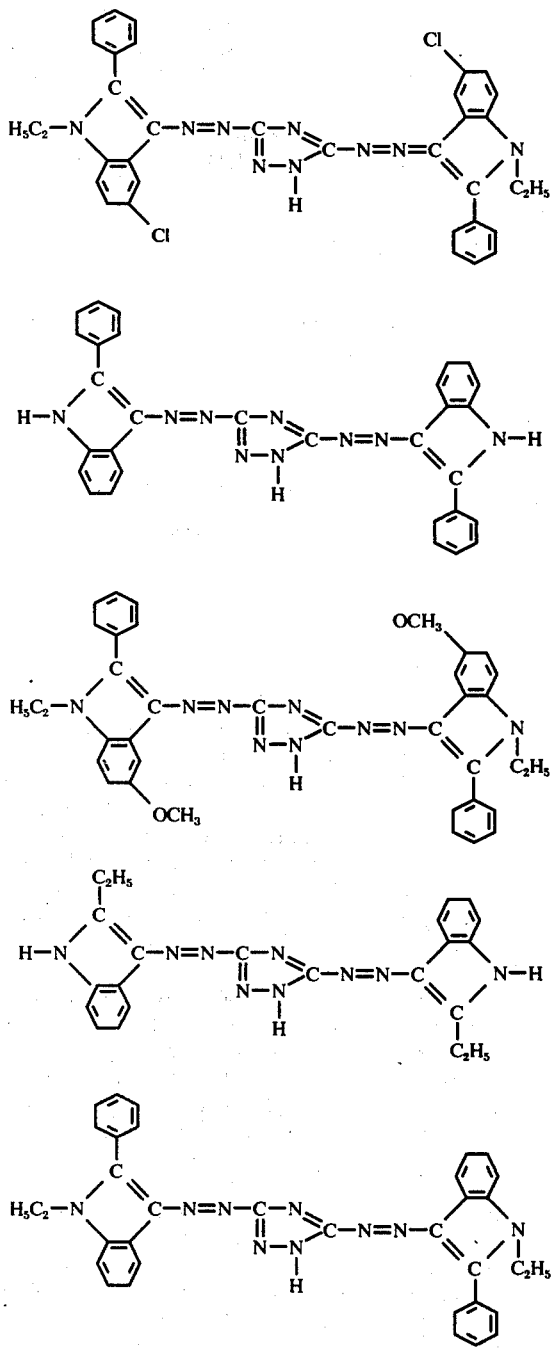

The azo dyes expressed by the general formula (1) are also described in Japanese Patent Nos. 233,714 and 233,715. However, we have found that the color changing indicator compositions for the gaseous sterilization containing said dyes as coloring materials possess excellent characteristics required for indicators for the sterilization using gaseous ethylene oxide, particularly excellent in color developing properties (change of the hue and strength of the color developed). Furthermore, they are remarkably excellent in regard to the properties required for printing ink and coating compositions. 0.5 – 5% by weight of said azo dye, based on the total weight of the color changing indicator composition can be used.

Hydrophobic polymers include, for example, nitrocellulose, ethyl cellulose, polyvinyl butyral, polyamide, rosin modified maleic resin, shellac, cellulose propionate, acrylic resins and the like. And also, hydrophobic polymers may include resins soluble in lower alkyl alcohols having from 1 to 6 carbon atoms. Further, if in any dry resin state, they have hydrophobic properties, such resins can be used, even if they are nominally hydrophilic resins. The hydrophobic polymer is used in amounts of from 10 to 50% by weight, based on the total weight of the color changing indicator composition.

Solvents include, for example, lower alcohols having from 1 to 6 carbon atoms, Cellosolve (Trade Mark for monoalkylether of ethylene glycol), or mixtures thereof. Furthermore, when an adjustment of the viscosity, etc. of the color changing indicator composition is necessary to make it suitable for coating or printing use, mixed solvents prepared by mixing aromatic hydrocarbons, such as, benzene, xylene, toluene and the like; a lower alkyl ester having from 1 to 4 carbon atoms of acetic acid, such as, ethyl acetate and the like; ketones, such as, methyl ethyl ketone and the like, or mixtures thereof, can be used in addition to solvents hereinbefore described. Said solvents or mixed solvents are used in amounts of from 30 to 85% by weight, based on the total weight of the color indicator composition.

A suitable catalyst is preferably added to facilitate the reaction of gaseous ethylene oxide with said composition coated or printed on a hermetically sealed material to be sterilized. Preferred catalysts are acidic and include phosphoric acid, p-toluene sulfonic acid, citric acid, malonic acid and maleic acid. The amount of the catalyst to be added is from 1 to 5% by weight, based on the total weight of the color changing indicator composition.

Further, suitable fillers are preferably added to facilitate the permeation of gaseous ethylene oxide into the film of the color changing indicator composition. Preferred fillers are silica, barium sulfate, clay, magnesium carbonate and calcium carbonate. The amount of the filler to be added is from 1 to 10% by weight, based on the total weight of the color changing indicator composition.

The resin hereinbefore described in blended into the solvent or the mixed solvent to prepare a polymer vehicle, and an azo dye described above is dissolved in said vehicle.

The catalyst and/or the filler can also be added, if necessary.

If the particle size of the filler is very fine as with colloidal silica, it may be used without requiring any pretreatment and be stirred, but if the particles are coarse, the filler should previously be ground with the above described polymer vehicle to be used and then the dispersed filler is added to the indicator composition. Although the color changing indicator composition may thus be prepared, other auxiliary materials such as paraffine wax, polyolefin wax, etc., maybe added to adjust the qualities of the composition. The color changing indicator compositions thus prepared are suitable for carrying out Flexographic printing and Gravure printing and the like.

Color changes of said dye compounds may occur by a reaction with gaseous ethylene oxide, but any desirable color change may be also possible if more than two kinds of said dyes are used in combination, or if other dyes or pigments which do not change in color by reactions with ethylene oxide are used in combination. As a pigment, for instance, Cyanine Blue, Watchung Red and Benzidine Yellow show base colors in blue, red and yellow, respectively. If the pigments are used in combination with the azo dyes, after the reaction with gaseous ethylene oxide, the color of the color changing indicator composition indicates the complementary color of the base color of a pigment used and the developed color of an azo dye used. For example, in combination with the azo dye whose color may change from yellow to red by the reaction of the azo dye with the gaseous ethylene oxide, with said Cyanine Blue, the color of the combination turns green first and then changes to violet after the reaction.

Embodiments of this invention are illustrated in detail in the following Examples. It should be understood that this invention is, however, in no way limited by the Examples, which are given only for the purpose of illustration of this invention.

EXAMPLE 1

20 parts by weight of butyral resin [Eslec BL-1 (Trade Mark), produced by Sekisui Chemical Industry Co., Ltd.] was dissolved in a mixture of 20 parts by weight of toluene, 48 parts by weight of methanol, and 10 parts by weight of Methyl Cellosolve (Trade Mark) to prepare a vehicle. 1 part by weight of the dye compound expressed by the following chemical formula with 1 part by weight of malonic acid as a catalyst was mixed by stirring with the above described vehicle in a mixer to prepare an ink composition.

100 parts by weight of said ink composition were diluted with 30 parts by weight of isopropyl alcohol and the resulting solution was used on a gravure printing machine for printing on a hermetically sealing to be sterilized.

A printed material thus obtained exhibited yellow color, and it was then sterilized using gaseous ethylene oxide (20% ethylene oxide : 80% carbon dioxide); the time for the sterilization was 6 hrs. at 60° C. The color of the ink composition film changed from yellow to orange after said sterilizing treatment, evidencing completion of the sterilization.

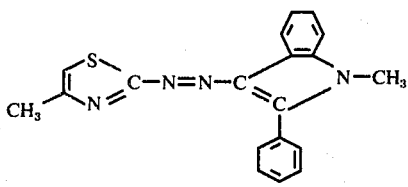

EXAMPLE 2

The same procedure as described in the preceding Example 1 was repeated for the preparation of an ink composition. The composition of said composition was as follows:

- 30 parts by weight of methanol
- 20 parts by weight of isopropyl alcohol
- 10 parts by weight of Methyl Cellosolve (Trade Mark)
- 38 parts by weight of rosin modified maleic resin [Teskid (Trade Mark) MRM-42, produced by Tokushima Oil Mills, Ltd.]
- 1 part by weight of the dye compound expressed by the chemical formula given below.

A red printed material of hermetically sealing was obtained by a Flexographic printing. The ink composition film changed in color to violet by a similar sterilizing treatment as described in Example 1.

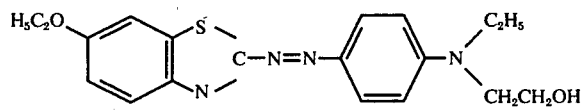

EXAMPLE 3

A mixture of 40 parts by weight of toluene, 15 parts by weight of methanol, 10 parts by weight of Methyl Cellosolve (Trade Mark), 30 parts by weight of polyamide resin [Polymide (Trade Mark) S-40 E, produced by Sanyo Chemical Industry Co., Ltd.], 1 part by weight of same dye compound as described in Example 1, 3 parts colloidal silica [Syloid (Trade Mark) 161, produced by Fuji-Davison Chemical Ltd.] was stirred in a mixer to prepare an ink composition.

20 parts by weight of a mixed solvent comprising methanol and toluene in a weight proportion of 40/60 of methanol to toluene was added to 100 parts of said ink composition fo printing on moisture-proof Cellophane (Trade Mark) To-Cello (Trade Mark) No. 300, produced by Tokyo Cellophane Co., Ltd. using a Gravure printing machine. The yellow ink composition film of the printed matter thus obtained changed color to orange, when said printed matter was sterilized by the similar treatment as described in Example 1.

Further, a green ink composition was obtained by mixing 20 parts by weight of the following pigment composition described hereunder with 100 parts by weight of the afore-mentioned ink composition. When said ink composition was used in printing and sterilized, the color of the ink composition film changed from green to violet.

Pigment Composition 1 part by weight of the dye compound used in the ink composition described hereinbefore was replaced by 5 parts by weight of Cyanine Blue, and the mixture was ground by a roll mill.

EXAMPLE 4

Several ink compositions were prepared by the same procedure as described in Example 1. Printed matters prepared with said ink compositions were sterilized with gaseous ethylene oxide, and the colour changes of the ink composition films are given in the following Table 1.

Table 1
| Azo Dyes | Colour before the treatment | Colour after the treatment with ethylene oxide |
|---|---|---|
| 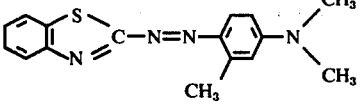 | red | bluish purple |
| 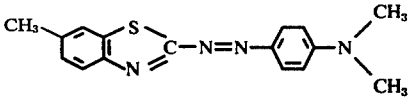 | red | bluish purple |
| 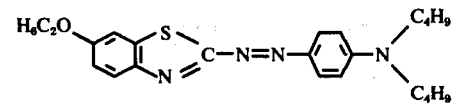 | red | bluish purple |
| 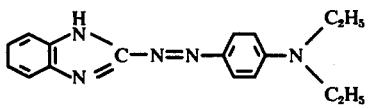 | red | violet |
| 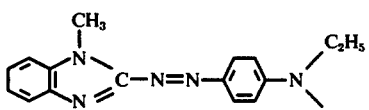 | red | violet |
| 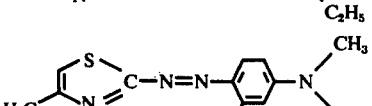 | red | violet |
| 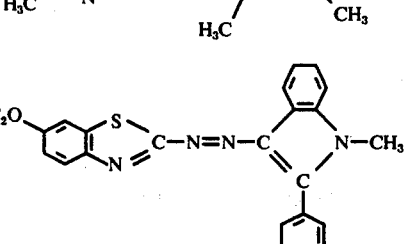 | yellow | red |
|  | yellow | reddish orange |
| 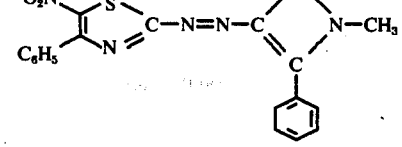 | red | reddish violet |
| 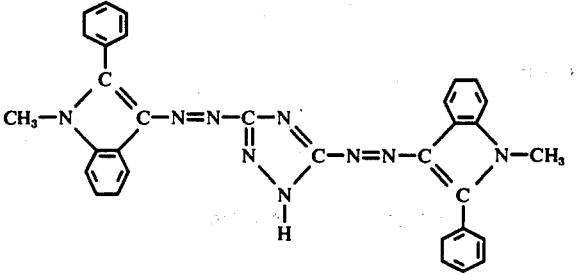 | yellow | red |

Table 1-continued

| Azo Dyes | Colour before the treatment | Colour after the treatment with ethylene oxide |
|---|---|---|
| [structure] | yellow | red |
| [structure] | red | violet |
| [structure] | yellow | red |
| [structure] | orange | red |
| [structure] | orange | reddish tint |
| [structure] | orange | reddish tint |

Table 1-continued

| Azo Dyes | Colour before the treatment | Colour after the treatment with ethylene oxide |
|---|---|---|
| | red | violet |
| | red | violet |
| | red | violet |

What is claimed is:

1. A process for detecting the completion of a sterilizing treatment of a medical or a surgical instrument in which a gaseous alkylene oxide is the sterilizing agent, which comprises exposing to said alkylene oxide the material to be sterilized and a color changing indicator composition, which indicator composition visibly exhibits a color change when exposed to said alkylene oxide, and maintaining said alkylene oxide in contact with said material and said indicator composition at least until said color change occurs in said indicator composition, said color changing indicator composition comprising from 1 to 5% by weight of an azo dye represented by the following formula

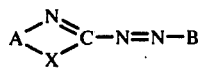

wherein A represents an ethylene residual group, an o-phenylene residual group, or

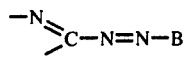

with proviso that —N is linked with X, while —C with N in the formula (1), respectively, which is further enabled to have an undissociative group as a substituent; X represents

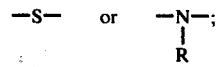

B represents an aniline-derivative residual group which can be coupled to the para-position or an enamine residual group having the formula,

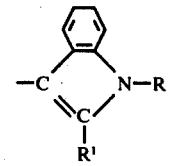

and the both groups are further enabled to have an undissociative group as a substituent, said R represents a hydrogen atom or a lower alkyl group having from 1 to 3 carbon atoms, said $R^1$ represents a hydrogen atom, a lower alkyl group having from 1 to 3 carbon atoms or a phenyl group, said undissociative group represents a lower alkyl group having from 1 to 3 carbon atoms, an alkoxy group having from 1 to 3 carbon atoms, —$R^2$—OH, chlorine, a phenyl group or a nitro group, wherein $R^2$ represents an alkylene group having from 1 to 3 carbon atoms, from 10 to 50% by weight of a hydrophobic polymer and from 30 to 85% by weight of a solvent or mixed solvent.

2. The process of claim 1 wherein the azo dye is a member selected from the group consisting of
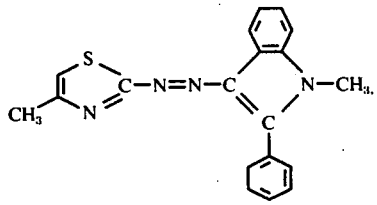
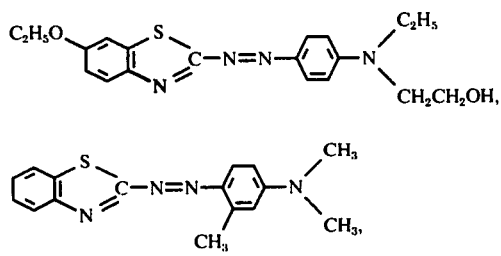
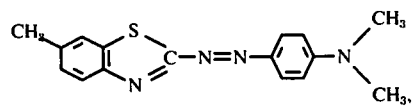
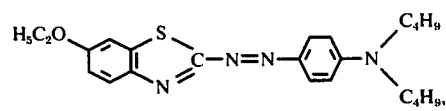
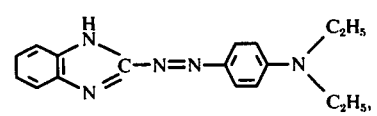
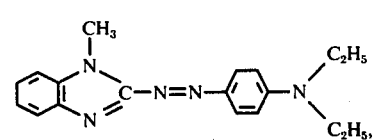
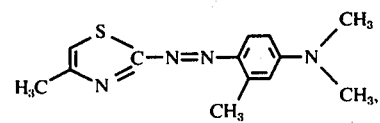
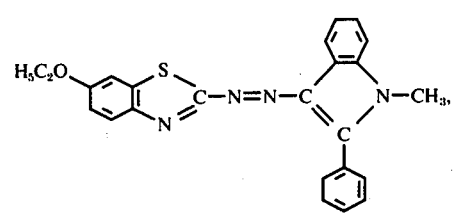
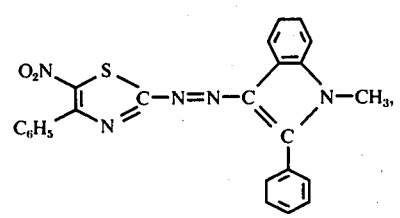
-continued
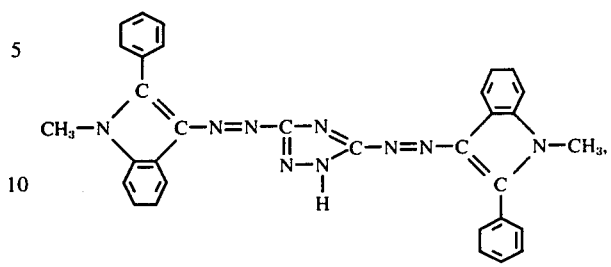
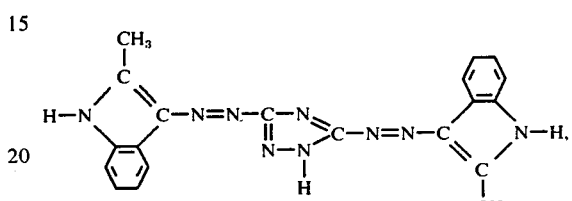
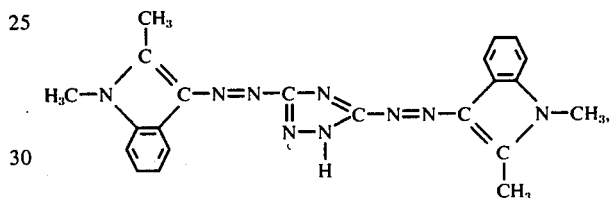
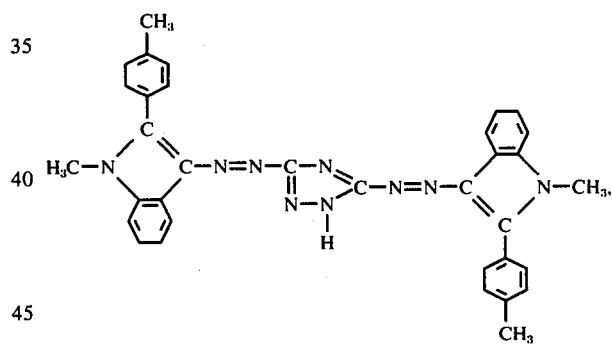
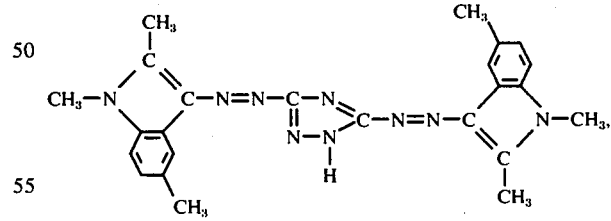
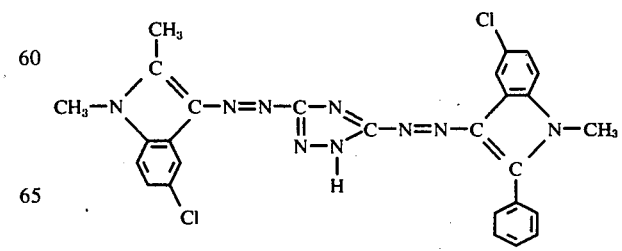

-continued

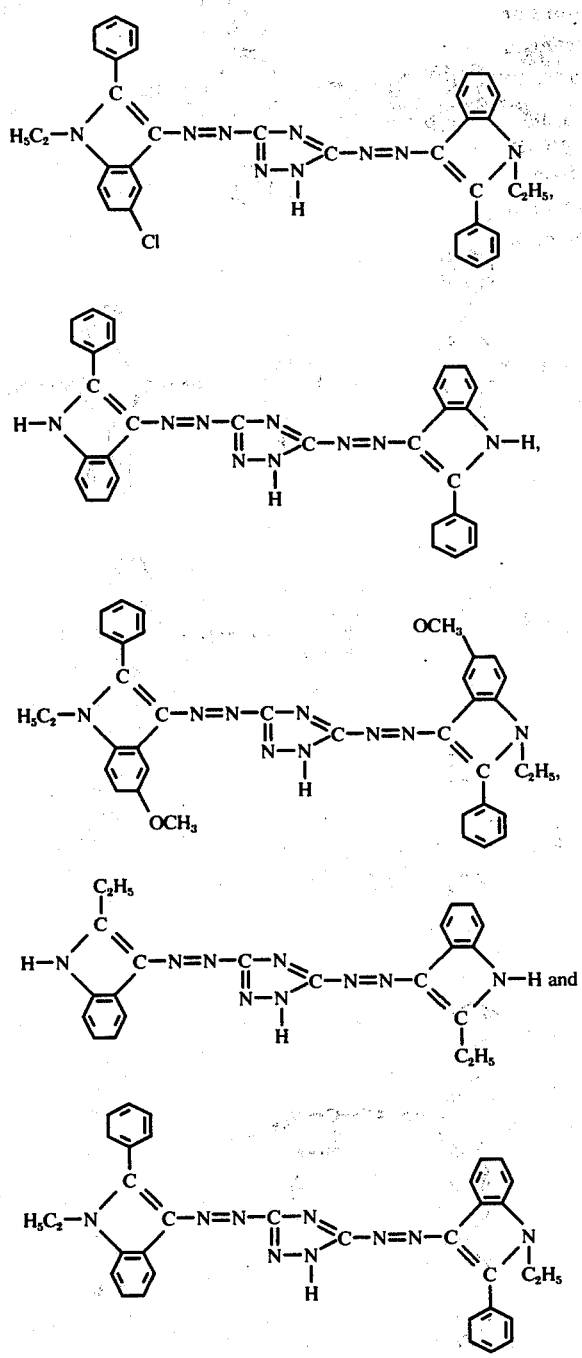

3. The process of claim 1 wherein the hydrophobic polymer is at least one member selected from the group consisting of nitrocellulose, ethyl cellulose, polyvinyl butyral, polyamide, rosin modified maleic resin, shellac, cellulose propionate and an acrylate resin.

4. The process of claim 1 wherein the solvent is at least one member selected from the group consisting of a lower alcohol having from 1 to 6 carbon atoms and Cellosolve.

5. The process of claim 1 wherein the mixed solvent is a mixture of at least one member selected from the group consisting of an aromatic hydrocarbons, a lower alkyl ester having from 1 to 4 carbon atoms of acetic acid and a ketone, with at least one member selected from the group consisting of a lower alcohol having from 1 to 6 carbon atoms and Cellosolve.

6. The process of claim 1 wherein the alkylene oxide is ethylene oxide.

7. The process of claim 1 wherein the color changing indicator composition comprises from 1 to 5% by weight of an azo dye, from 10 to 50% by weight of a hydrophobic polymer, from 30 to 85% by weight of a solvent or mixed solvent and from 1 to 5% by weight of a catalyst.

8. The process of claim 1 wherein the color changing indicator composition comprises from 1 to 5% by weight of an azo dye, from 10 to 50% by weight of a hydrophobic polymer, from 30 to 85% by weight of a solvent or mixed solvent and from 1 to 10% by weight of a filler.

9. The process of claim 1 wherein the color changing indicator composition comprises from 1 to 5% by weight of an azo dye, from 10 to 50% by weight of a hydrophobic polymer, from 30 to 85% by weight of a solvent or a mixed solvent, from 1 to 5% by weight of a catalyst and from 1 to 10% by weight of a filler.

10. In a process for detecting the completion of a sterilizing treatment of a medical or a surgical instrument in the hermetically sealed sterilized condition with gaseous alkylene oxide by color change of a color changing indicator composition printed or coated on a herrmetically sealing material, the improvement wherein the color changing indicator composition comrises from 1 to 5% by weight of an azo dye represented by the following formula

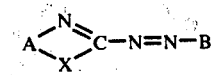

wherein A represents an ethylene residual group, an o-phenylene residual group, or

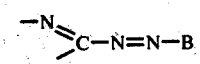

with proviso that —N is linked with X, while —C with N in the formula (1), respectively, which is further enabled enabled to have an undissociative group as a substituent; X represents —S—or

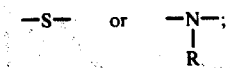

B represents an aniline-derivative residual group which can be coupled to the para-position or an enamine residual group having the formula,

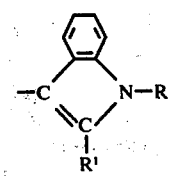

and the both groups are further enabled to have an undissociative group as a substituent, said R represents a hydrogen atom or a lower alkyl group having from 1 to 3 carbon atoms, said $R^1$ represents a hydrogen atom, a lower alkyl group having from 1 to 3 carbon atoms or a phenyl group, said undissociative group represents a lower alkyl group having from 1 to 3 carbon atoms, an alkoxyl group having from 1 to 3 carbon atoms, $-R^2-OH$, chlorine, a phenyl group or a nitro group, wherein $R^2$ represents an alkylene group having from 1 to 3 carbon atoms, from 10 to 50% by weight of a hydrophobic polymer and from 30 to 85% by weight of a solvent or mixed solvent.

11. The process of claim 10 wherein the azo dye is a member selected from the group consisting of

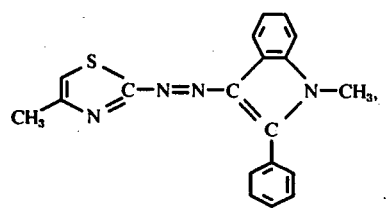
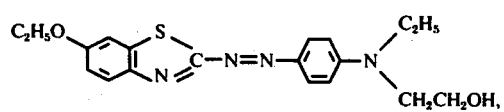
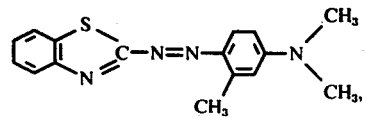
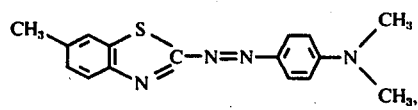
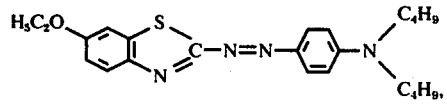
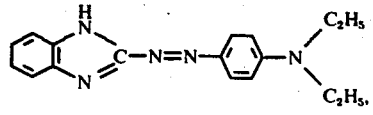
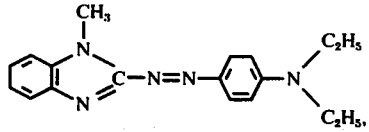
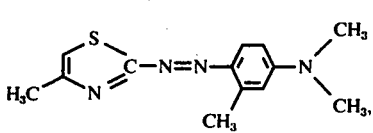
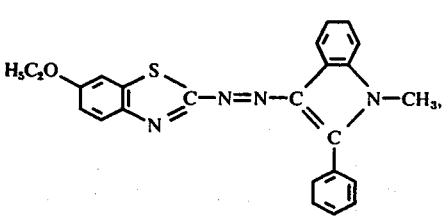

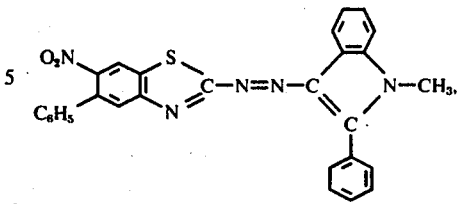
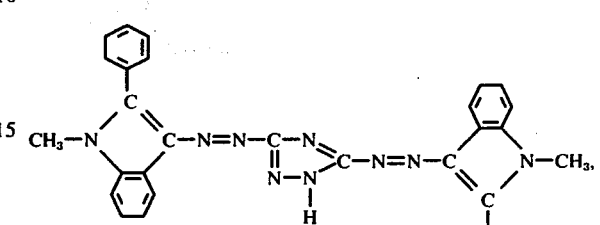
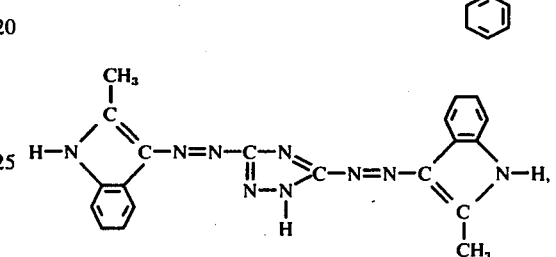
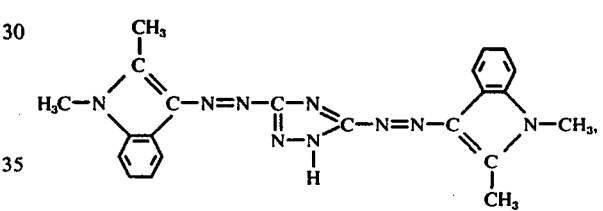
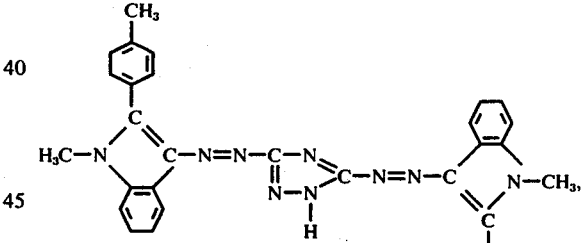
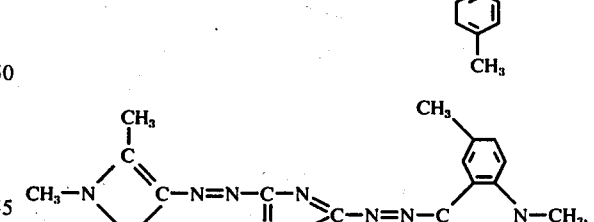
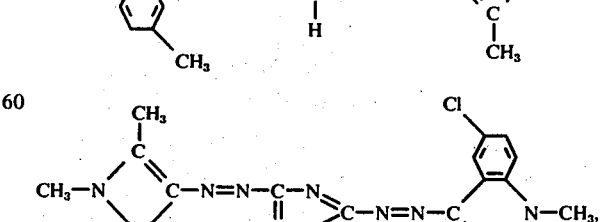

-continued

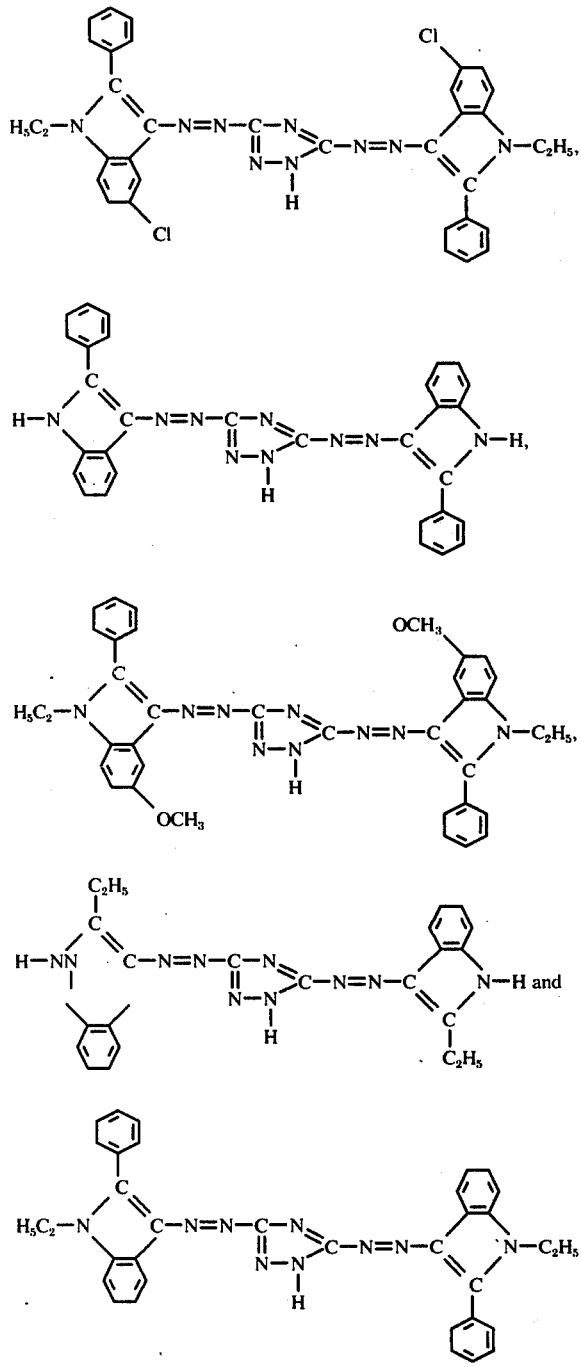

12. The process of claim 10 wherein the color changing indicator composition contains another dye or pigment which does not change in color when contacted with said alkylene oxide.

13. The process of claim 10 wherein the hydrophobic polymer is at least one member selected from the group consisting of nitrocellulose, ethyl cellulose, polyvinyl butyral, polyamide, rosin modified maleic resin, shellac, cellulose propionate and an acrylate resin.

14. The process of claim 10 wherein the solvent is at least one member selected from the group consisting of a lower alcohol having from 1 to 6 carbon atoms and Cellosolve.

15. The process of claim 10 wherein the mixed solvent is a mixture of at least one member selected from the group consisting of an aromatic hydrocarbon, a lower alkyl ester having from 1 to 4 carbon atoms of acetic acid and a ketone, with at least one member selected from the group consisting of a lower alcohol having from 1 to 6 carbon atoms and Cellosolve.

16. The process of claim 10 wherein the alkylene oxide is ethylene oxide.

17. The process of claim 10 wherein the color changing indicator composition comprises from 1 to 5% by weight of an azo dye, from 10 to 50% by weight of a hydrophobic polymer, from 30 to 85% by weight of a solvent or mixed solvent and from 1 to 5% by weight of a catalyst.

18. The process of claim 10 wherein the color changing indicator composition comprises from 1 to 5% by weight of an azo dye, from 10 to 50% by weight of a hydrophobic polymer, from 30 to 85% by weight of a solvent or mixed solvent and from 1 to 10% by weight of a filler.

19. The process of claim 10 wherein the color changing indicator composition comprises from 1 to 5% by weight of an azo dye, from 10 to 50% by weight of a hydrophobic polymer, from 30 to 85% by weight of a solvent or a mixed solvent, from 1 to 5% by weight of a catalyst and from 1 to 10% by weight of a filler.

20. The process of claim 10 wherein the color changing indicator composition comprises from 1 to 5% by weight of the azo dye having the formula

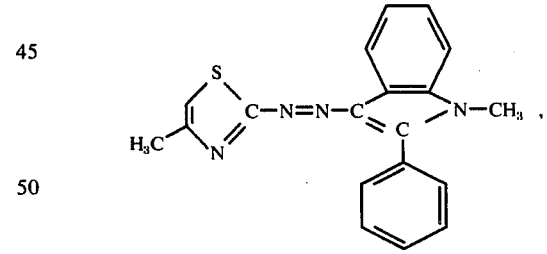

from 10 to 50% by weight of butyral resin, from 30 to 85% by weight of a mixed solvent comprising toluene, methanol and Methyl Cellosolve, and from 1 to 5% by weight of malonic acid.

* * * * *